United States Patent
Shin et al.

(10) Patent No.: US 8,682,419 B2
(45) Date of Patent: Mar. 25, 2014

(54) CIRCUIT AND METHOD FOR COMPENSATING FOR AN ELECTRODE MOTION ARTIFACT

(75) Inventors: Kun Soo Shin, Seongnam-si (KR); Jong Pal Kim, Seoul (KR); Jin Sang Hwang, Suwon-si (KR); Hyun Tai Hwang, Yongin-si (KR)

(73) Assignee: Samsung Electronics Co., Ltd., Suwon-Si (KR)

(*) Notice: Subject to any disclaimer, the term of this patent is extended or adjusted under 35 U.S.C. 154(b) by 668 days.

(21) Appl. No.: 12/659,699

(22) Filed: Mar. 17, 2010

(65) Prior Publication Data

US 2010/0179443 A1 Jul. 15, 2010

Related U.S. Application Data

(62) Division of application No. 11/372,373, filed on Mar. 10, 2006, now Pat. No. 7,711,414.

(30) Foreign Application Priority Data

Oct. 5, 2005 (KR) ........................ 10-2005-0093497

(51) Int. Cl.
*A61B 5/0402* (2006.01)
(52) U.S. Cl.
USPC .......................................... 600/509; 600/508
(58) Field of Classification Search
USPC .................................... 600/300, 509; 607/27
See application file for complete search history.

(56) References Cited

U.S. PATENT DOCUMENTS

| 4,494,552 A | 1/1985 | Heath ............................ 128/696 |
| 5,020,541 A * | 6/1991 | Marriott ........................ 600/536 |
| 5,197,467 A | 3/1993 | Steinhaus et al. ............. 128/419 |

(Continued)

FOREIGN PATENT DOCUMENTS

| EP | 1426771 | 6/2004 |
| KR | 10-2003-0082675 | 10/2003 |

(Continued)

OTHER PUBLICATIONS

Patrick S. Hamilton and Michael G. Curley, Adaptive removal of motion artifact, Oct. 30, 2007-Nov. 2, 1997, $19^{th}$ International Conference-IEEE/EMBS, pp. 297-299.

(Continued)

*Primary Examiner* — Carl H Layno
*Assistant Examiner* — Jennifer Ghand
(74) *Attorney, Agent, or Firm* — Staas & Halsey LLP

(57) ABSTRACT

A circuit and method for compensating for an electrode motion artifact in which the electrode motion artifact is generated because impedance between a subject and a measuring electrode changes during measurement of the subject's biosignal, and the electrode motion artifact can be differentially measured and an electrocardiogram signal can be compensated by introducing a predetermined voltage or an electric current to the subject. A circuit and method for compensating electrode motion artifact, which can differentially measure the difference information between impedance components by introducing a predetermined voltage or electric current to a subject, in association with the electrode motion artifact. In this instance, the impedance component is a component of electrode motion artifact and the electrode motion artifact is generated when measuring a biosignal.

7 Claims, 4 Drawing Sheets

(56) References Cited

U.S. PATENT DOCUMENTS

| | | | |
|---|---|---|---|
| 5,247,939 A | 9/1993 | Sjoquist et al. | 128/697 |
| 5,632,280 A | 5/1997 | Leyde et al. | 128/696 |
| 2002/0032383 A1 | 3/2002 | Weil et al. | 600/484 |
| 2002/0183797 A1 | 12/2002 | Kaiser et al. | 607/27 |
| 2003/0171661 A1 | 9/2003 | Tong | 600/300 |
| 2005/0113703 A1 | 5/2005 | Farringdon et al. | 600/509 |
| 2007/0010750 A1 | 1/2007 | Ueno et al. | |

FOREIGN PATENT DOCUMENTS

| | | |
|---|---|---|
| KR | 10-0493714 | 5/2005 |
| KR | 10-2005-0061756 | 6/2005 |
| WO | 2005/032367 | 4/2005 |

OTHER PUBLICATIONS

John G. Webster, Medical Instrumentation: Application and Design, 1998, John Wiley & Sons Inc., Third Edition, pp. 89, 96, 233-235, 241, and 244.

Korean Notice of Allowance issued Apr. 15, 2008 in corresponding Korean Patent Application No. 10-2005-0093497.

U.S. Restriction Requirement mailed Sep. 30, 2008 related to parent U.S. Appl. No. 11/372,373.

U.S. Office Action mailed Dec. 11, 2008 related to parent U.S. Appl. No. 11/372,373.

U.S. Final Office Action mailed May 13, 2009 related to parent U.S. Appl. No. 11/372,373.

U.S. Advisory Action mailed Jul. 1, 2009 related to parent U.S. Appl. No. 11/372,373.

U.S. Advisory Action mailed Jul. 10, 2009 related to parent U.S. Appl. No. 11/372,373.

U.S. Office Action mailed Sep. 15, 2009 related to parent U.S. Appl. No. 11/372,373.

U.S. Notice of Allowance mailed Dec. 18, 2009 related to parent U.S. Appl. No. 11/372,373.

* cited by examiner

CIRCUIT AND METHOD FOR COMPENSATING FOR AN ELECTRODE MOTION ARTIFACT

CROSS-REFERENCE TO RELATED APPLICATION

This application is a Divisional of application Ser. No. 11/372,373 filed on Mar. 10, 2006, now issued as U.S. Pat. No. 7,711,414, which claims the priority of Korean Patent Application No. 10-2005-93497, filed on Oct. 5, 2005, in the Korean Intellectual Property Office, the disclosure of which is incorporated herein by reference.

BACKGROUND OF THE INVENTION

1. Field of the Invention

The present invention relates to a circuit and method for compensating for an electrode motion artifact in which the electrode motion artifact is generated because impedance between a subject and a measuring electrode changes during measurement of the subject's biosignal, and the electrode motion artifact can be differentially measured and an electrocardiogram signal can be adjusted by introducing a predetermined voltage Vc or an electric current Vi into the subject.

2. Description of Related Art

A biometric measurement device can collect and analyze a minute action current, an electrical change of the action current, and the like. An action current is generated within a subject, such as from the heart of a human body. A biometric measurement device can indicate various biometric information about a corresponding subject in forms that a predetermined medical examiner can recognize. The biometric measurement device connects an electrode and a subject that is a target for medical test and interprets the change of a voltage measured by the electrode to collect a biosignal.

In this case, the biometric measurement device has to physically contact the electrode on the surface of the subject to collect a biosignal. Accordingly, the change of impedance between the subject and the electrode inevitably occurs because of the characteristics in which the subject continually moves and the problem in which the electrode misses a predetermined measurement point.

The change of impedance may function as noise, such as an electrode motion artifact, with respect to biosignals collected in the biometric measurement device. Accordingly, the change of impedance may distort a waveform with respect to measurement results or interfere with measurement of generated information.

The most obvious case of the electrode motion artifact described above is when the attachment of an electrode is faulty. As an example of a configuration for recognizing the fault, U.S. Pat. No. 5,632,280 (hereinafter, referred to as 'conventional art') discloses a circuit monitoring whether the attachment of the electrode is faulty by using an amplifier having a gain of one and a voltage source. It is illustrated in FIG. 1.

FIG. 1 is a diagram illustrating monitoring with respect to a faulty attachment of an electrode in the conventional art.

As illustrated in FIG. 1, uni-directional electric current Ip is supplied to a plurality of electrodes in the conventional art. In the conventional art, output signal Vi may be calculated by 'Vi=Vprobe+Ip*(Rf1+Rf2+Rp)+Ip*(Z1+Z2)'. Also, an impedance component between electrodes and skin is measured by 'Z1+Z2'. Accordingly, it is possible to monitor whether the attachment of an electrode is a fault by using the change of the impedance component 'Z1+Z2'.

However, since a biosignal is differentially measured, an impedance component substantially contained in the biosignal, such as a component of electrode motion artifact, may be defined by the impedance difference between electrodes, such as Z1−Z2. Accordingly, the electrode motion artifact has to be removed. However, a method of measuring impedance component 'Z1+Z2' may not remove electrode motion artifact 'Z1−Z2' from the differentially measured biosignal.

BRIEF SUMMARY

An aspect of the present invention provides a circuit and method for compensating for an electrode motion artifact, which can differentially measure the difference information between impedance components by introducing a predetermined voltage Vc or an electric current Ic into a subject.

An aspect of the present invention also provides a circuit and method for compensating electrode motion artifact, which can differentially measure an impedance component with respect to a subject and input impedance, when performing compensation processing with respect to an output signal outputted from a differential amplifier. In this instance, the subject is a target for measurement and the input impedance is connected to each electrode.

An aspect of the present invention also provides a circuit and method for compensating for an electrode motion artifact, which can compensate an electrocardiogram signal more accurately and easily since a motion artifact component influencing an electrocardiogram signal and a measured impedance component are outputted in the same form.

According to an aspect of the present invention, there is provided a method for compensating electrode motion artifact, the method including: measuring an electrocardiogram signal including an electrode motion artifact signal; forming a first impedance between a subject and a first electrode attached to the subject and forming a second impedance between the subject and a second electrode attached to the subject; measuring the difference between the first impedance and the second impedance by using a carrier signal; and adjusting the electrocardiogram signal by using a signal of the measured difference between the first impedance and the second impedance.

Also, according to another aspect of the present invention, there is provided a circuit for compensating electrode motion artifact, including: a carrier signal source oscillating with a carrier signal; a first electrode and a second electrode measuring a voltage or an electric current of a subject to which the carrier signal is introduced; a third electrode introducing the oscillated carrier signal into a subject; a differential amplifier differentially detecting or amplifying signals from the first electrode and the second electrode and outputting an output signal; and an electrocardiogram extraction unit removing the electrode motion artifact signal from the output signal and selectively extracting only the electrocardiogram signal.

According to another aspect of the present invention, there is provided a circuit for compensating for an electrode motion artifact, including: a carrier signal source oscillating a carrier signal; a first electrode and a second electrode measuring a voltage or an electric current of the subject to which the carrier signal is introduced; a third electrode introducing the oscillated carrier signal into a subject; a differential amplifier differentially detecting or amplifying signals from the first electrode and the second electrode and outputting an output signal, the output signal including an electrocardiogram signal and an electrode motion artifact measured from the subject; and an electrocardiogram extraction unit removing the electrode motion artifact signal from the output signal and selectively extracting only the electrocardiogram signal.

According to another aspect of the present invention, there is provided a circuit for compensating electrode motion artifact, including: a carrier signal source oscillating a carrier signal; a first electrode and a second electrode measuring a voltage or an electric current of a subject to which the carrier signal is introduced; a third electrode introducing the oscillated carrier signal to the subject; a differential amplifier differentially detecting or amplifying signals from the first electrode and the second electrode and outputting an output signal, the output signal including an electrocardiogram signal and an electrode motion artifact measured from the subject; a filter passing the output signal and selectively detecting the electrocardiogram signal belonging to a particular frequency band; and a feedback controller returning an output signal excluding the detected electrocardiogram signal to the differential amplifier.

According to another aspect of the present invention, there is provided a circuit for compensating electrode motion artifact, including: a first electrode and a second electrode measuring a voltage or an electric current of a subject; a third electrode grounding the subject; a differential amplifier differentially detecting or amplifying signals from the first electrode and the second electrode and outputting an output signal, the output signal including an electrocardiogram signal and an electrode motion artifact measured from the subject; and an electrocardiogram extraction unit removing the electrode motion artifact signal from the output signal and selectively extracting only the electrocardiogram signal, the electrocardiogram extraction unit comprising: a demodulator demodulating the modulated electrode motion artifact by the carrier signal; and a filter filtering a particular frequency band of the output signal to detect the demodulated electrode motion artifact and electrocardiogram signal. A carrier signal oscillated from a predetermined carrier signal source is introduced to the differential amplifier.

According to other aspects of the present invention, there are provided computer-readable recording media encoded with processing instructions for executing the aforementioned embodiments of the present invention.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF EMBODIMENTS

Figure 1:
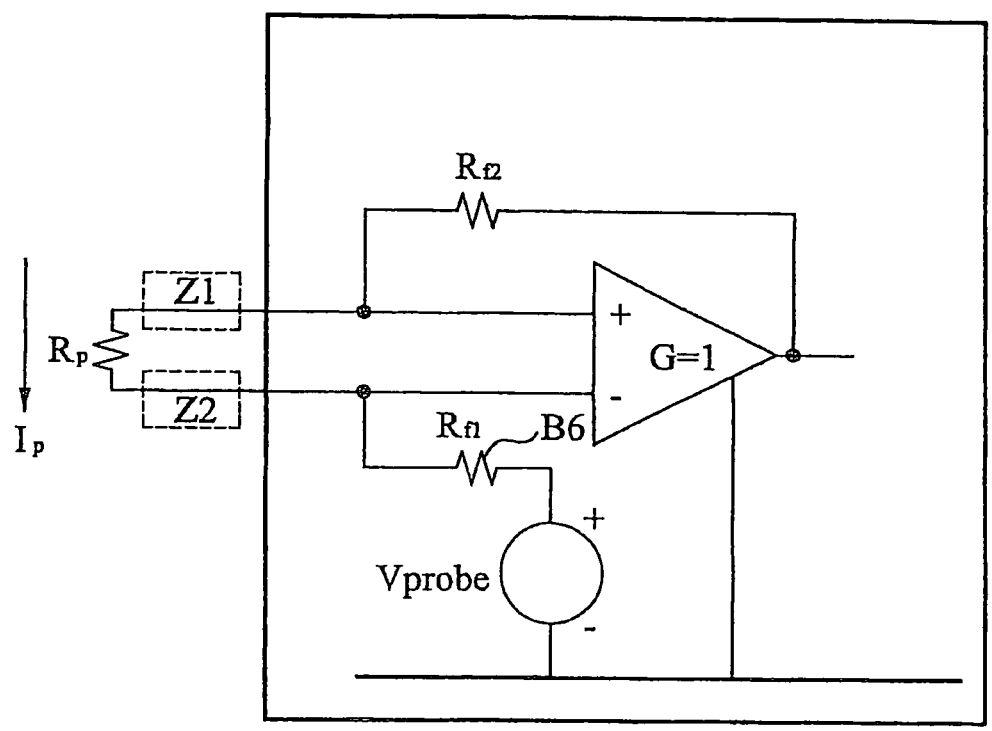
FIG. 1 is a diagram illustrating monitoring with respect to a faulty attachment of an electrode in conventional art.

Reference will now be made in detail to embodiments of the present invention, examples of which are illustrated in the accompanying drawings, wherein like reference numerals refer to the like elements throughout. The embodiments are described below in order to explain the present invention by referring to the figures.

An "electrode motion artifact" as used in the present specification may be a kind of noise generated because the impedance between a subject and an electrode changes by any motion of the subject, when measuring a biosignal from the subject, such as a human body or the like. The electrode motion artifact described above functions as noise in an electrocardiogram (ECG) signal. Also, the electrode motion artifact may distort a waveform of measurement results and interfere with the measurement of a heart rate or analysis of a state of a heart.

Accordingly, when measuring an ECG signal, it is necessary to improve the accuracy of measurement results by classifying and removing the electrode motion artifact. In particular, the present embodiment introduces a predetermined voltage Vc or an electric current Ic into a subject which is a target for measuring an ECG signal, and compensates measurement results distorted because of electrode motion artifact.

An electrode motion artifact compensating circuit includes a biosignal compensating circuit and a signal compensating circuit. In this instance, the biosignal compensating circuit introduces the voltage Vc or the electric current Ic into a subject as input to the subject and collects output signal Vi from the subject as output with respect to the subject. The signal compensating circuit outputs an ECG signal associated with the subject through predetermined compensation processing with respect to the output signal Vi.

Figure 2:
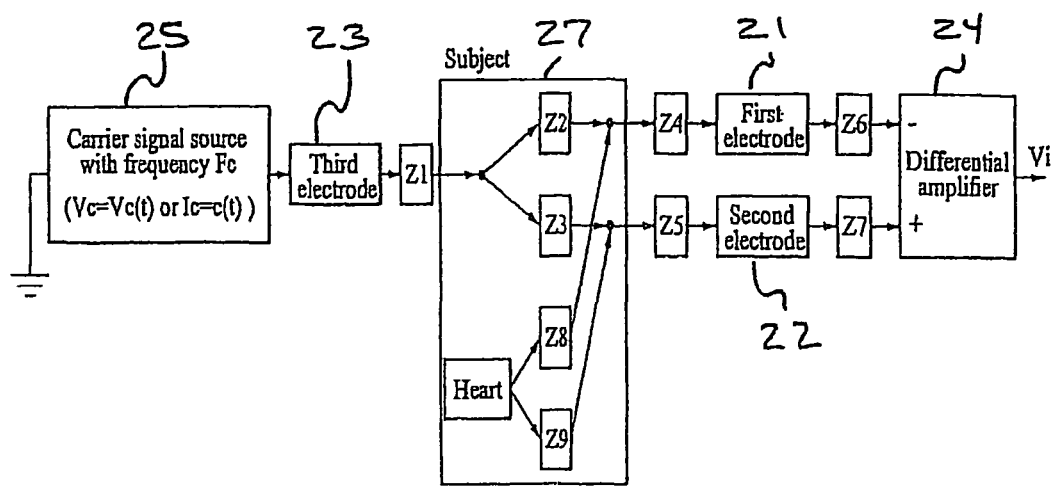
FIG. 2 is a diagram explaining an electrode motion artifact compensating circuit according to an embodiment of the present invention.
Figure 2:
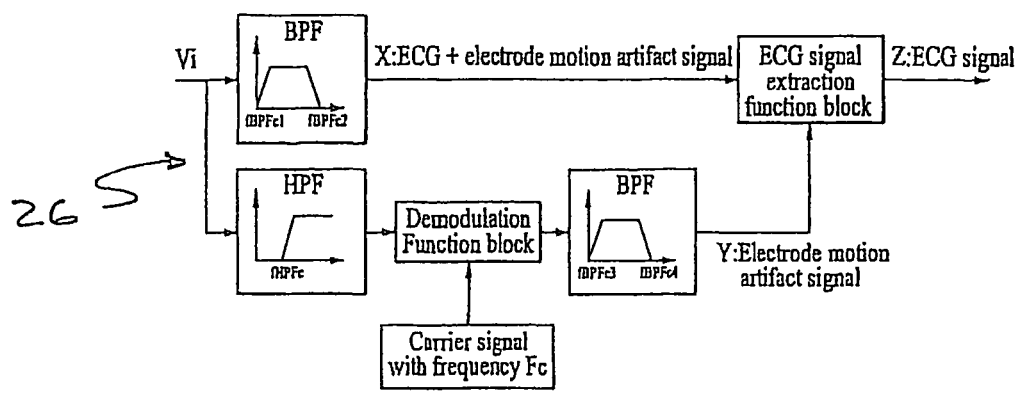

FIG. 2 is a diagram explaining an embodiment of an electrode motion artifact compensating circuit according to the present invention.

The electrode motion artifact compensating circuit measures a biosignal from a subject. In particular, in the present embodiment, carrier signal Fc of electric current Ic or voltage Vc having predetermined frequency is introduced into a subject. This is to separate, that is, compensate an electrode motion artifact signal from output signal Vi. In this case, the output signal Vi is outputted according to measurement processing of the subject.

For this, as illustrated in FIG. 2, the electrode motion artifact compensating circuit may include respective first to third electrodes 21, 22, and 23, a differential amplifier 24, a carrier signal source 25, an ECG extraction unit 26, and various external and internal impedance components such as Z1 to Z9.

Initially, the first electrode and the second electrode measure a voltage or an electric current of a subject 27 introduced with a carrier signal. The carrier signal is generated by the carrier signal source which is an oscillating means. Also, the carrier signal is introduced into the subject via another electric unit attached to the subject, that is, via the third electrode.

Also, the first electrode and the second electrode collect a predetermined biosignal from the subject. Accordingly, the first electrode and the second electrode may be a test instrument directly contacting the surface of the skin of a human body which is a subject in collecting information such as an ECG or the like. That is, the first electrode and the second electrode function to detect and obtain a minutely generating biosignal such as an ECG from a subject, and to transfer the obtained biosignal to the differential amplifier to amplify the biosignal by a predetermined scale.

In the present embodiment, the first electrode and the second electrode are respectively connected to an inverting node and a non-inverting node of the differential amplifier. Also, the biosignal collected from the subject is inputted in each node.

Also, impedance component Z6 and impedance component Z7 may be respectively positioned between the first and second electrodes and nodes of the differential amplifier.

Also, the impedance components Z6 and Z7 help the collected biosignal to be safely inputted into the differential amplifier without loads. The size of impedance components Z6 and Z7 may be determined according to a circuit embodying environment.

Z1 is impedance formed between the third electrode and a position of the third electrode attached onto a subject. Z4 is impedance formed between the first electrode and a position of the first electrode attached onto the subject. Z5 is impedance formed between the second electrode and a position of the second electrode attached onto the subject. Also, Z2 is impedance formed between the position of the third electrode attached onto the subject and the position of the first electrode attached onto the subject. Z3 is impedance formed between the position of the third electrode attached onto the subject and the position of the second electrode attached onto the subject. Also, Z8 is impedance formed between the heart and the position of the first electrode attached onto the subject. Z9 is impedance formed between the heart and the position of the second electrode attached onto the subject.

The differential amplifier functions to differentially detect or amplify signals from the first electrode and the second electrode, and to output an output signal. Specifically, the differential amplifier generates an ECG signal and an electrode motion artifact signal from a subject introduced with a carrier signal via the third electrode, as an output signal. In this instance, the electrode motion artifact signal is in a modulated form to be transferred to a predetermined frequency band by a carrier signal.

Also, the differential amplifier includes an inverting node, a non-inverting node, and an output node. The inverting node is connected to the first electrode, the non-inverting node connected to the second electrode, and the output node differentially amplifies biosignals collected and inputted via the first and second electrodes and outputs output signal Vi. Namely, the differential amplifier amplifies minute biosignals measured from the first electrode and the second electrode in a predetermined amplitude, processes an output signal, and outputs processed output signal Vi via the output node. The output signal Vi may be displayed in the form that a medical examiner may recognize via a predetermined display.

The output signal Vi differentially amplified by a differential amplifier may include an ECG signal measured from a subject, an electrode motion artifact signal by electrode motion artifact, and carrier signal Fc. In this instance, the carrier signal Fc is a frequency component associated with voltage Vc or electric current Ic introduced into the subject. Accordingly, an electrode motion artifact compensating circuit executes compensation processing to remove the electrode motion artifact signal. This is to detect only a biosignal of a subject such as an ECG signal which is substantially necessary information. In the present embodiment, carrier signal Fc of electric current Ic or voltage Vc having predetermined frequency is introduced to a subject. This is to more easily classify an electrode motion artifact signal when performing the compensation processing. In this case, the carrier signal may be used in demodulation or modulation with respect to an electrode motion artifact signal measured from the subject.

The carrier signal source introduces carrier signal Fc of voltage Vc or electric current Ic to a subject. For example, the carrier signal source may generate variable voltage Vc or variable electric current Ic at a frequency of 250 Hz and introduce the same to a subject as a carrier signal. In this case, introducing the voltage Vc or the electric current Ic as a carrier signal is to transfer Y signal including an electrode motion artifact signal from output signal Vi to a high frequency band and classify only an electrode motion artifact signal through demodulation. The carrier signal of the voltage Vc or the electric current Ic may be introduced to a subject via a predetermined electrode such as the third electrode.

Also, the electrode motion artifact compensating circuit may generate a predetermined potential difference in a plurality of positions of a subject contacting the first electrode and the second electrode.

The generation of the potential difference in the subject is to measure the difference information between impedance components, that is, Z6−Z7. An ECG signal mixed with electrode motion artifact may be compensated by excluding a static difference component and using a dynamic difference component from signals of Z6−Z7 measured above. Detailed description related thereto will be described later. In this case, the size of the generated potential difference may be in proportion to Z6−Z7, which is the difference information between the impedance components. Accordingly, a medical examiner may approximately infer the size of the electrode motion artifact generated when a corresponding biosignal is measured, by using only the size of the potential difference.

Also, impedance component Z1 in a random size may be positioned between a carrier signal source and a subject. Accordingly, an excessive size of voltage Vc or electric current Ic may not be directly introduced to the subject. The impedance component Z1 may be a resistor or a capacitor which is directly inserted into an embodiment circuit. Also, the impedance component Z1 may indicate internal impedance which occurs between electrodes connecting a carrier signal source and a subject.

The ECG extraction unit functions to remove only an electrode motion artifact signal from output signal Vi, and identify and detect only an ECG signal from an output signal.

As illustrated in FIG. 2, the ECG extraction unit includes devices such as a filter portion and a demodulator portion. Also, the ECG extraction unit performs compensation processing via the devices.

First, the ECG extraction unit passes output signal Vi to a band pass filter (BPF) of the filter portion, and detects an X signal including an ECG signal and an electrode motion artifact signal from the output signal Vi. Namely, the BPF selectively detects an X signal including an ECG signal and an electrode motion artifact signal. In this instance, the X signal develops in a low frequency band. For example, the BPF may detect an ECG signal and an electrode motion artifact signal developing in the frequency band between 0.5 and 50 Hz.

Also, the ECG extraction unit: passes output signal Vi to a high band pass filter (HPF) of a filter portion and identifies only an electrode motion artifact signal developing in a high frequency band; and demodulates the identified electrode motion artifact signal by using carrier signal Fc in a frequency of 250 Hz. In this manner, the ECG extraction unit transfers the modulated electrode motion artifact signal to a particular frequency band. Namely, the ECG extraction unit may transfer the electrode motion artifact signal identified through these procedures to a frequency band equivalent to that of the detected X signal, and make an environment having an identical frequency.

Next, the ECG extraction unit also passes the identified electrode motion artifact signal to the BPF of the filter portion, identifies an electrode motion artifact signal developing in the frequency band between 0.5 and 50 Hz, and detects the identified electrode motion artifact signal as a Y signal.

After this, the ECG extraction unit may identify and output an ECG signal from the X signal through compensation processing using the detected X signal and Y signal.

Namely, the ECG extraction unit may obtain ECG signal Z excluding an electrode motion artifact signal from X and Y signals via adaptive filters. The adaptive filters may include an LMS adaptive filter, a Kalman adaptive filter, an RLS adaptive filter, and the like.

Figure 3:
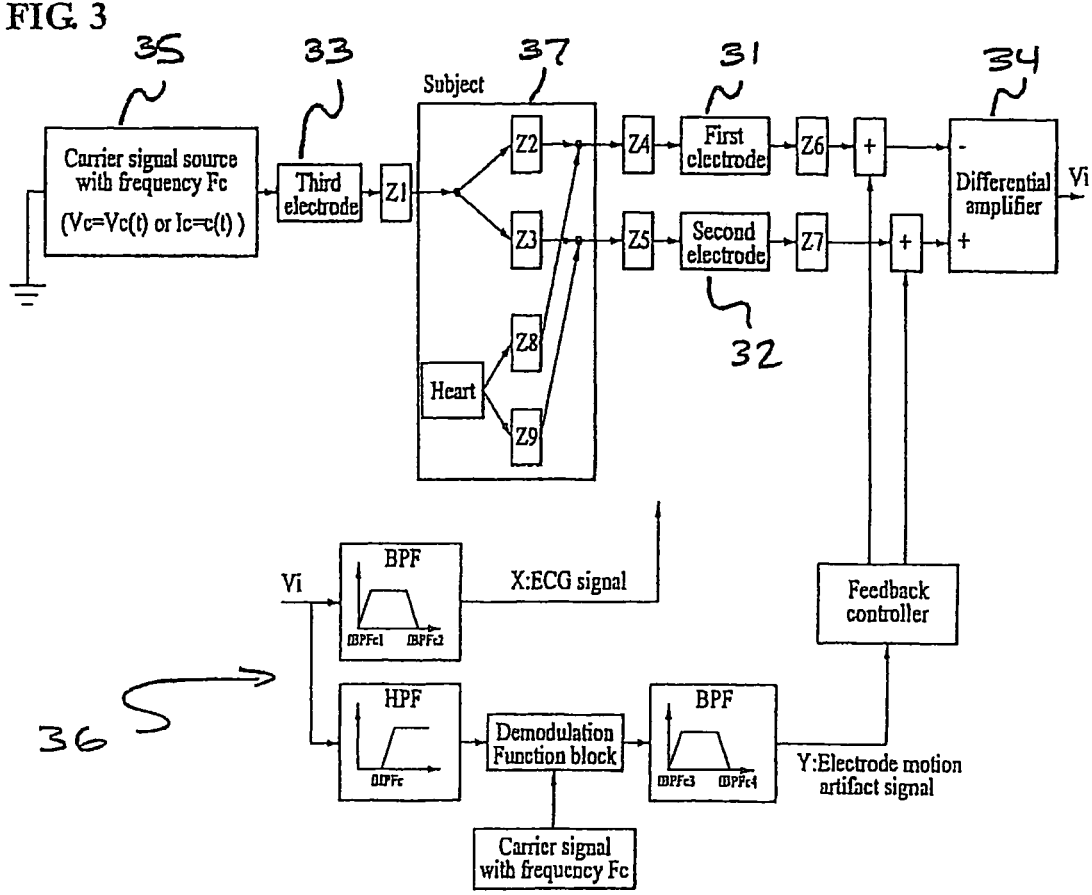
FIG. 3 is a diagram explaining an electrode motion artifact compensating circuit according to another embodiment of the present invention.

FIG. 3 is a diagram explaining another embodiment of an electrode motion artifact compensating circuit according to the present invention.

As illustrated in FIG. 3, the electrode motion artifact compensating circuit may include respective first to third electrodes 31, 32, and 33, a differential amplifier 34, a carrier signal source 35, an ECG extraction unit 36, and various external and internal impedance components such as Z1 to Z9.

FIG. 3 shows that output signal Vi' including an electrode motion artifact signal is returned to an electrode motion artifact compensating circuit and the compensation processing with respect to output signal Vi is simplified. In this instance, the output signal Vi is outputted from a differential amplifier by an action of the returned output signal Vi'.

In the present embodiment, as output signal Vi outputted from a differential amplifier passes only a BPF of a filter portion, an ECG signal may be selectively detected. Also, in the present embodiment, an output signal excluding the ECG signal, that is, an output signal including an electrode motion artifact signal is returned to a differential amplifier via a predetermined feedback controller.

As illustrated in FIG. 3, the electrode motion artifact compensating circuit may further include a feedback controller in the aforementioned electrode motion artifact compensating circuit of FIG. 2. The feedback controller returns an output signal including an electrode motion artifact signal to the electrode motion artifact compensating circuit. Through this, an ECG signal may be selectively detected by only passing later outputted output signal Vi to a BPF. Accordingly, in the present embodiment, the compensation process using X and Y signals described in the embodiment of FIG. 2 may be omitted. Accordingly, when detecting an ECG signal, compensation processing may be more simplified.

Figure 4:
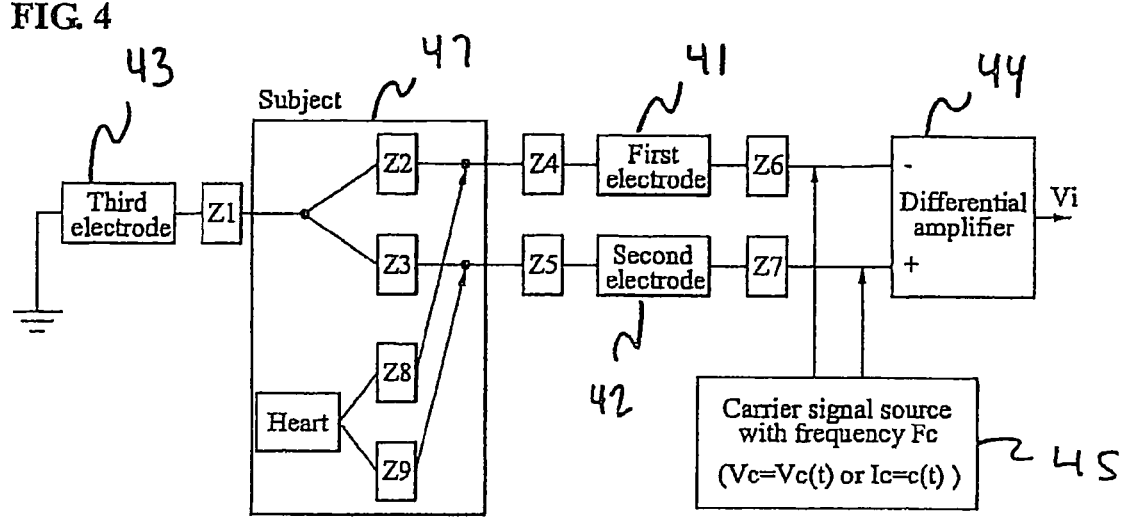
FIG. 4 is a diagram explaining an electrode motion artifact compensating circuit according to still another embodiment of the present invention.
Figure 4:
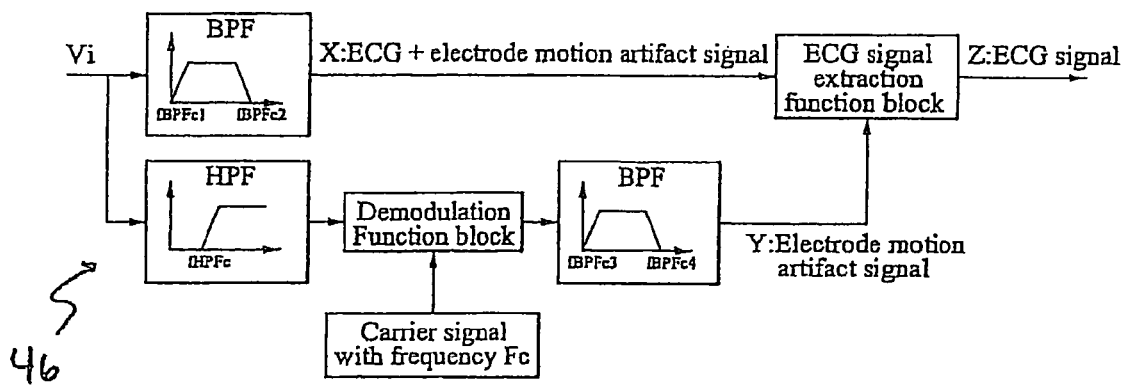

FIG. 4 is a diagram explaining still another embodiment of an electrode motion artifact compensating circuit according to the present invention.

As illustrated in FIG. 4, the electrode motion artifact compensating circuit may include respective first to third electrodes 41, 42, and 43, a differential amplifier 44, a carrier signal source 45, an ECG extraction unit 46, and various external and internal impedance components such as Z1 to Z9.

FIG. 4 shows that a third electrode attached to a subject grounds the subject while directly introducing a carrier signal oscillated from a carrier signal source to a differential amplifier. Namely, in the present embodiment, a position of introducing a carrier signal may be changed according to a circuit embodying environment.

When detecting an ECG signal, an ECG extraction unit of FIG. 4 passes output signal Vi to a BPF of a filter portion and detects an X signal including an ECG signal and an electrode motion artifact signal. Also, the ECG extraction unit passes output signal Vi to an HPF of a filter portion and performs demodulation by a carrier signal. The ECG extraction unit identifies an electrode motion artifact signal via a series of processing described above and detects the identified electrode motion artifact signal as a Y signal. After this, the ECG extraction unit may identify and output the ECG signal from the X signal through compensation processing using the detected X and Y signals.

The electrode motion artifact compensating circuit according to the above-described embodiments of the present invention introduces a carrier signal of voltage Vc or an electric current Ic to a subject when performing compensation processing with respect to output signal Vi outputted from a differential amplifier. Accordingly, an electrode motion artifact signal may be differentially measured.

According to the above-described embodiments of the present invention, there is provided a circuit and method for compensating for an electrode motion artifact, which can differentially measure the difference information between impedance components by introducing predetermined voltage Vc or an electric current Ic into a subject, in association with electrode motion artifact. In this instance, the impedance component is a component of the electrode motion artifact and the electrode motion artifact is generated when measuring a biosignal.

Also, according to the above-described embodiments of the present invention, there is provided a circuit and method for compensating for an electrode motion artifact, which can differentially measure an impedance component with respect to a subject and input impedance, when performing compensation processing with respect to an output signal outputted from a differential amplifier. In this instance, the subject is a target for measurement and the input impedance connects each electrode.

Also, according to the above-described embodiments of the present invention, there is provided a circuit and method for compensating for electrode motion artifact, which can compensate an electrocardiogram signal more accurately and easily as a motion artifact component influencing an electrocardiogram signal and a measured impedance component are outputted in the same form.

Embodiments of the present invention can also be implemented as computer-readable code on a computer-readable recording medium. The computer-readable recording medium is any data storage device that can store data which can be thereafter read by a computer system. Examples of the computer-readable recording medium include magnetic storage mediums (such as read-only memory (ROM), floppy disks, and hard disks), optical reading mediums (such as CD-ROMs and DVDs), and carrier waves (such as data transmission through the Internet).

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A method of compensating for an electrode motion artifact, the method comprising:
    measuring an electrocardiogram signal including an electrode motion artifact signal;
    forming a first impedance between a subject and a first electrode attached to the subject and forming a second impedance between the subject and a second electrode attached to the subject;
    measuring a difference between the first impedance and the second impedance using a carrier signal; and adjusting the electrocardiogram signal using a signal of the measured difference between the first impedance and the second impedance.

2. The method of claim 1, wherein, in the adjusting, signals from the first electrode and the second electrode are differentially amplified to compensate the electrocardiogram signal.

3. The method of claim 1, wherein the carrier signal is introduced to the subject from a predetermined carrier signal source, and
wherein, in the measuring, the difference between the first impedance and the second impedance is measured via demodulation or modulation using the carrier signal.

4. The method of claim 1, wherein, in the adjusting, the electrocardiogram signal is adjusted by using a dynamic difference component, excluding a static difference component between the first impedance and the second impedance, among signals of the measured difference between the first impedance and the second impedance.

5. A non-transitory computer-readable recording medium comprising computer readable code to control a processing device to implement a method of compensating for an electrode motion artifact, the method including:

measuring an electrocardiogram signal including an electrode motion artifact signal;
forming a first impedance between a subject and a first electrode attached to the subject and forming a second impedance between the subject and a second electrode attached to the subject;
measuring a difference between the first impedance and the second impedance using a carrier signal; and
adjusting the electrocardiogram signal using a signal of the measured difference between the first impedance and the second impedance.

6. The method of claim 1, wherein the adjusting comprises adjusting the measured electrocardiogram signal including the electrode motion artifact signal so as to produce an electrocardiogram signal with minimized electrode motion artifacts.

7. The non-transitory computer-readable recording medium of claim 5, wherein the adjusting comprises adjusting the measured electrocardiogram signal including the electrode motion artifact signal so as to produce an electrocardiogram signal with minimized electrode motion artifacts.

* * * * *